(12) United States Patent
Gronau et al.

(10) Patent No.: US 11,154,645 B2
(45) Date of Patent: Oct. 26, 2021

(54) PRODUCING AND DOSING A SUBSTITUATE DURING BLOOD TREATMENT

(71) Applicant: Fresenius Medical Care Deutschland GmbH, Bad Homburg (DE)

(72) Inventors: Soeren Gronau, Nauheim (DE); Juergen Haecker, Neu Anspach (DE); Ralf Mueller, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 632 days.

(21) Appl. No.: 13/798,758

(22) Filed: Mar. 13, 2013

(65) Prior Publication Data

US 2013/0240443 A1    Sep. 19, 2013

Related U.S. Application Data

(60) Provisional application No. 61/610,485, filed on Mar. 14, 2012.

(30) Foreign Application Priority Data

Mar. 14, 2012   (DE) .................... 10 2012 004 970.6

(51) Int. Cl.
*A61M 1/16* (2006.01)
*A61M 1/34* (2006.01)

(52) U.S. Cl.
CPC ............ *A61M 1/16* (2013.01); *A61M 1/1605* (2014.02); *A61M 1/3462* (2013.01); *A61M 1/3465* (2014.02); *A61M 2205/3331* (2013.01); *A61M 2205/3334* (2013.01)

(58) Field of Classification Search
USPC ............................ 210/321.65, 646; 604/6.09
See application file for complete search history.

(56) References Cited

U.S. PATENT DOCUMENTS 4,702,829 A    10/1987  Polaschegg et al.
5,808,181 A *   9/1998  Wamsiedler ........ A61M 1/3455
                                              210/646
(Continued)

FOREIGN PATENT DOCUMENTS

DE           3444671 C2    11/1988
DE         19700466 A1     7/1998
(Continued)

*Primary Examiner* — Hayden Brewster
(74) *Attorney, Agent, or Firm* — Fish & Richardson P.C.

(57) ABSTRACT

The present disclosure relates to methods for dosing a substituate produced by a blood treatment apparatus. Dosing for the present disclosure is via a hydraulic system of the blood treatment apparatus, the hydraulic system having at least one dialysis liquid supply line which leads into a dialyzer and at least one substituate line. Regulating or controlling the size of the share which passes through the second filtration stage is performed by affecting at least one conveying apparatus and/or at least one flow limitation device and/or a flow divider valve, which are each located or which each operate in the dialysis liquid supply line and/or the substituate line and/or in the branch line which connects the dialysis liquid Supply line with the substituate line. The present disclosure further relates to a control device, a blood treatment apparatus, and a medical functional apparatus.

14 Claims, 8 Drawing Sheets

(56) References Cited

U.S. PATENT DOCUMENTS

| | | | |
|---|---|---|---|
| 6,039,877 A * | 3/2000 | Chevallet | A61M 1/1656 210/111 |
| 6,280,632 B1 | 8/2001 | Polaschegg | |
| 6,607,697 B1 * | 8/2003 | Muller | 422/44 |
| 6,855,122 B1 * | 2/2005 | Ohta | A61M 1/3621 422/46 |
| 7,850,856 B2 * | 12/2010 | Zhang | A61M 1/342 210/143 |
| 2003/0073945 A1 | 4/2003 | Diang | |
| 2006/0200064 A1 * | 9/2006 | Gross | A61M 1/16 604/5.01 |
| 2006/0254982 A1 * | 11/2006 | Kopperschmidt | 210/646 |
| 2007/0249982 A1 | 10/2007 | Daniel et al. | |
| 2009/0101550 A1 * | 4/2009 | Muller | A61M 1/16 210/87 |
| 2010/0106071 A1 * | 4/2010 | Wallenborg | A61M 1/166 604/5.01 |
| 2010/0130906 A1 * | 5/2010 | Balschat | A61M 1/16 604/6.09 |
| 2013/0139901 A1 * | 6/2013 | Haecker | A61M 1/3643 137/15.05 |

FOREIGN PATENT DOCUMENTS

| | | |
|---|---|---|
| DE | 19832451 C1 | 8/1999 |
| DE | 102004026561 A1 | 12/2005 |
| DE | 102009024606 A1 | 12/2010 |
| DE | 102009048920 A1 | 4/2011 |
| DE | 102010032179 A1 | 1/2012 |
| EP | 0694312 A2 | 1/1996 |
| EP | 0763367 A1 | 3/1997 |
| EP | 0930080 A1 | 7/1999 |
| WO | WO 2008/125893 * | 10/2008 |
| WO | 2011063906 A1 | 6/2011 |
| WO | WO 2012010320 A1 * | 1/2012 |

* cited by examiner

PRODUCING AND DOSING A SUBSTITUATE DURING BLOOD TREATMENT

CROSS REFERENCE TO RELATED APPLICATIONS

This application claims the benefit of U.S. Provisional Patent Application No. 61/610,485, filed on Mar. 14, 2012, and German Patent Application No. 10 2012 004 970.6, filed on Mar. 14, 2012.

FIELD OF INVENTION

The present invention relates to a method for dosing, creating or providing a substituate which was produced by a blood treatment apparatus. In addition, the present invention relates to a control device as well as a blood treatment apparatus for executing this method. Furthermore, the present invention relates to a medical functional apparatus, a digital storage medium, a computer program product, as well as a computer program related to the method.

BACKGROUND OF INVENTION

From practice, extracorporeal blood treatment apparatuses and methods are known in which a substituate is added to the extracorporeal blood circuit. Frequently, the substituate is produced online, i.e. during the blood treatment session and usually by the blood treatment apparatus itself. For this, a part of the dialysis liquid which is usually also produced online is prompted to also pass through the membrane of a second filter or a second filtration stage after it has passed through the membrane of a first filter or a first filtration stage. After running through this second filtration (sterile filtration), the substituate gained that way may be added to the contents of the extracorporeal blood circuit at a predilution site and/or a postdilution site of the extracorporeal blood circuit upstream and downstream, respectively, from the dialyzer or the blood filter.

There are requirements with respect to the precision with which the substituate is added to the contents of the extracorporeal blood circuit. Thus, state-of-the-art apparatuses as known from practice comprise a high-precision dosing apparatus for dosing the substituate which is completely (e.g. in the form of a membrane pump in a blood cassette) or partially (e.g. in the form of a pump tubing segment for a roller pump at a conventional blood tube set or integrated in a blood cassette) part of the blood tube set which is used for the blood treatment.

One object of the present invention is to propose a further method for dosing, creating or providing a substituate which was produced online. It is further an object of the present invention to propose a corresponding control device, a corresponding blood treatment apparatus, a corresponding medical functional apparatus, a digital storage medium, a computer program product as well as a computer program.

All advantages achievable by the method according to the present invention may in certain exemplary embodiments according to the present invention undiminishedly be also achieved with the above-mentioned apparatuses and devices.

Thus, according to the present invention, a method for dosing, creating or providing a substituate which was produced by a blood treatment apparatus is proposed. The method according to the present invention thereby takes place by a hydraulic system or a hydraulic section (hereafter in short: hydraulic system) of the blood treatment apparatus. The hydraulic system comprises at least one dialysis liquid supply line which leads into the dialysate chamber of a blood filter or a dialyzer (hereafter in short: dialyzer) or which supplies dialysis liquid to the dialyzer. The hydraulic system further comprises at least one substituate line as well as a first filtration stage and a second filtration stage.

The dialysis liquid supply line supplies fresh dialysis liquid to the dialyzer, whereas the dialysate drain line which is mentioned further below discharges used or waste dialysis liquid, also denoted as dialysate, out of the dialyzer.

The substituate line guides or conducts substituate being supplied to the interior or the contents of a blood circuit (substantially blood) used during the blood treatment for volume substitution, or it is provided herefor.

Optionally, the hydraulic system may further comprise a branch line connecting the dialysis liquid supply line with the substituate line. Optionally, the connection is achieved via the filtration stage which is located between the branch line and the substituate line and which is hereafter denoted as second filtration stage. The branch line leads into the second filtration stage, it is connected with it and/or it conducts fresh dialysis liquid into it. The term "filter" which is herein also used instead of "filtration stage" can be understood as a synonym of filtration stage. A filtration stage may in turn comprise or consist of several filters.

The method according to the present invention encompasses conveying a first fluid (or filtering the first fluid) through the first filtration stage which is upstream of the second filtration stage in flow direction and into the dialysis liquid supply line. Thereby, the fluid exits from the first filtration stage as a dialysis liquid which may be and/or is introduced in a dialyzer.

The method according to the present invention further encompasses (actively or passively) conducting a share or part (of a flow share or a volume share) of the dialysis liquid into the substituate line which attaches to or follows after a second filtration stage or is downstream thereof in fluid communication with it, for example, in that the substituate line follows to the second filtration stage or is being fed from it.

Upon passing through the second filtration stage, a substituate which can be and/or has been introduced into an extracorporeal blood circuit is being produced.

The method according to the present invention further encompasses regulating or controlling the share of the dialysis liquid (or the size of this share) which exits from the first filtration stage and which in the second filtration stage is filtered or passes through its membrane, or the share which is guided into a medical functional apparatus via the substituate line after having been filtered at the second filtration stage or which is provided to be guided into the extracorporeally conducted blood of a patient.

Regulating or controlling the share of the dialysis liquid or of the substituate which each are filtered in the second filtration stage or guided into the functional device (or into an extracorporeal blood circuit) takes place by affecting at least one conveying apparatus and/or at least one flow limitation device and/or a flow divider valve, which are each present in or affect the dialysis liquid supply line, the substituate line and/or the branch line.

Affecting may take place by known measures to actuate flow limitation apparatuses or conveying devices.

The control device according to the present invention, which may also be embodied as a regulating device, is provided, established, programmed and/or configured to control or regulate a blood treatment apparatus for or during execution of the method according to the present invention when interacting with the blood treatment apparatus. For this, it is during its use connected with the elements of the hydraulic system of the blood treatment apparatus which are to be controlled or regulated or it is in operative and/or signal connection with them.

The blood treatment apparatus according to the present invention comprises a hydraulic system, which comprises at least one dialysis liquid supply line and at least one substituate line. The hydraulic system may optionally comprise at least one branch line as described above. The blood treatment apparatus is embodied, provided and/or configured for executing the dosing method according to the present invention. In certain exemplary embodiments, it comprises the devices which are necessary herefor or it is connected with such devices in operative connection and/or signal connection.

The medical (i.e. provided for medical purposes) functional apparatus according to the present invention is provided to be used together with a blood treatment apparatus according to the present invention. It comprises its own substituate line and a substituate port or connection. The substituate port is provided to receive substituate produced by the hydraulic system of the blood treatment apparatus from the substituate line of the hydraulic system. The medical functional apparatus does not comprise an apparatus which is arranged and/or provided for dosing the substituate which passes over from the substituate line of the functional apparatus into a blood-conducting line of the functional apparatus.

The digital storage medium according to the present invention, in particular in the form of a disk, CD or DVD or EPROM, with electronically readable control signals may interact with a programmable computer system such that the mechanical steps of the method according to the present invention are prompted.

The computer program product according to the present invention comprises a program code stored on a machine-readable storage device for prompting the mechanical steps of the method according to the present invention when the computer program product is executed or run on a computer.

The term "machine-readable storage device," as used herein, denotes in certain exemplary embodiments of the present invention a storage device which contains data or information which is interpretable by software and/or hardware. The storage device may be a data storage device such as a disk, a CD, DVD, a USB stick, a flashcard, an SD card and the like.

The computer program according to the present invention comprises a program code for prompting the mechanical steps of the method according to the present invention when the computer program runs on a computer.

It applies to the digital storage medium, the computer program product according to the present invention and the computer program according to the present invention that all, a few or some of the mechanically executed steps of the method according to the present invention are prompted.

In all of the following exemplary embodiments, the use of the expression "may be" or "may have" and so on, is to be understood synonymously with "preferably is" or "preferably has," respectively, and so on, and is intended to illustrate an exemplary embodiment according to the present invention.

Exemplary embodiments according to the present invention may comprise one or more of the features named hereafter.

In some exemplary embodiments according to the present invention, dosing the substituate is a mechanical producing, enabling or effecting the separation or provision of a concrete substituate flow (e.g. in milliliters per minute) or a concrete volume of substituate liquid. The substituate flow which is defined this way by the hydraulic system, or the substituate volume which is defined this way, corresponds in certain exemplary embodiments according to the present invention to the flow or volume which leaves the hydraulic system and enters a medical functional apparatus, for example via a substituate port of the hydraulic system, which is connected with the blood treatment for the purpose of the blood treatment session.

In certain exemplary embodiments according to the present invention, the conveying device is a pump, a pressure pump, a flow pump, a volume pump or the like.

In some exemplary embodiments according to the present invention, the flow limitation device is a throttle, a flow divider valve, a proportional valve, a tube squeeze valve or the like.

In some exemplary embodiments of the method according to the present invention or the blood treatment apparatus according to the present invention, all apparatuses or devices for dosing the substituate which is being or which was actually introduced into the extracorporeal blood circuit are exclusively part of the hydraulic system or embedded herein. This applies in particular to the conveying devices which are mentioned in connection with the exemplary embodiments according to the present invention as described herein such as a pump, a pressure pump, a flow pump or a volume pump or the like. This also applies in particular to the flow limitation devices which are mentioned in connection with the exemplary embodiments according to the present invention as described herein such as a throttle, a flow divider valve, a proportional valve, a tube squeeze valve or the like.

In certain exemplary embodiments according to the present invention, the second filtration stage is inserted in the dialysis liquid supply line so that all dialysis liquid, which is being supplied to the dialyzer, has flown also through the second filtration stage regardless of whether it was filtered therein or not.

In some exemplary embodiments according to the present invention, the hydraulic system comprises a second filtration stage in the branch line of the dialysis liquid supply line, or as end point of the branch line, or it leads into it.

In certain exemplary embodiments according to the present invention, the hydraulic system comprises at least one flush line. A "flush line" is according to the present invention understood as a line which begins at the outlet of the dialysis liquid chamber of the second filtration stage. It may exemplarily be connected with the dialysate drain line of the dialyzer. According to the present invention, a flush line may also be denoted or used as a rinse line, flush line or scour line.

In some exemplary embodiments according to the present invention, the hydraulic system comprises at least one bypass line branching off the substituate line to the flush. It can exemplarily be connected with the dialysate drain line of the dialyzer.

In some exemplary embodiments according to the present invention, "flushing" is understood as a temporary rinsing, flushing or scouring. It can be intended to remove air or particles from the filter. A valve opened herefor may subsequently be closed, and the substitution can be continued.

In certain exemplary embodiments according to the present invention, the hydraulic system comprises a flow divider valve in the dialysis liquid supply line downstream of or "behind" the first filtration stage.

In some exemplary embodiments according to the present invention, the hydraulic system comprises a proportional valve in the dialysis liquid supply line downstream of or behind the second filtration stage.

In certain exemplary embodiments according to the present invention, the hydraulic system comprises a proportional valve in the substitute line downstream of the second filtration stage.

In certain exemplary embodiments according to the present invention, the hydraulic system comprises (at least) one proportional valve before or upstream of the second filtration stage and/or behind the second filtration stage.

In some exemplary embodiments according to the present invention, the hydraulic system comprises at least one apparatus to measure the flow (flow measurement) in the dialysis liquid supply line.

In certain exemplary embodiments according to the present invention, the hydraulic system comprises at least one apparatus to measure the flow in the branch line and upstream of or "in front of" the second filtration stage.

In some exemplary embodiments according to the present invention, the hydraulic system comprises at least one apparatus to measure the flow in the substitute line and downstream of the second filtration stage.

In certain exemplary embodiments according to the present invention, the hydraulic system comprises at least one pre-pressure pump in the dialysis liquid supply line and behind the first filtration stage, but upstream of a branch point at which a branch line branches off the dialysis liquid supply line and/or upstream of the second filtration stage.

In some exemplary embodiments according to the present invention, the hydraulic system comprises at least one apparatus for measuring the pre-pressure (pre-pressure measurement) in the dialysis liquid supply line and upstream of the second filtration stage.

In certain exemplary embodiments according to the present invention, the hydraulic system comprises at least one pre-pressure pump in the branch line and upstream of the second filtration stage.

In some exemplary embodiments according to the present invention, the hydraulic system comprises at least one pressure pump in the substitute line and downstream of the second filtration stage.

In certain exemplary embodiments according to the present invention, the hydraulic system comprises at least one volume pump in the branch line and upstream of the second filtration stage.

In certain exemplary embodiments according to the present invention, the hydraulic system comprises at least one temperature sensor downstream of the pressure pump or the volume pump.

In some exemplary embodiments according to the present invention, the hydraulic system comprises at least one apparatus for monitoring the pressure (pressure monitoring) downstream of the volume pump.

In certain exemplary embodiments according to the present invention, the hydraulic system comprises at least one apparatus for measuring the pre-pressure (pre-pressure measurement) upstream from the volume pump.

In some exemplary embodiments according to the present invention, the hydraulic system comprises at least one particle filter in the substitute line upstream or downstream of the volume pump.

In certain exemplary embodiments according to the present invention, the hydraulic system comprises at least one blood detector in the substitute line.

In some exemplary embodiments according to the present invention, the substitute which has been produced as described herein by the hydraulic system is introduced into the blood present in the extracorporeal blood circuit without any further measures which serve or could serve a dosing of the substitute which is introduced or is to be introduced into the extracorporeal blood circuit.

In certain exemplary embodiments according to the present invention, the method further encompasses regulating or controlling the size of the share of dialysis liquid which passes through the second filtration stage, based on preset information regarding the desired substitute flow or substituate volume, or based on the data obtained during the treatment from which in a step of the method information about the required substitute flow is calculated. Thereby, regulating or controlling consists of affecting at least one conveying device and/or at least one flow limitation device and/or a flow divider valve, which are each present or act in the dialysis liquid supply line and/or the substitute line and/or in the branch line, or it encompasses such affecting.

In particular exemplary embodiments according to the present invention, the blood treatment apparatus comprises a control or regulating device which is configured for executing the dosing method according to the present invention.

In some exemplary embodiments according to the present invention of the blood treatment apparatus, the second filtration stage is integrated in the dialysis liquid supply line and/or is being flown through by all dialysis liquid supplied to the dialyzer. Thereby, a proportional valve is arranged in the dialysis liquid supply line downstream of the second filtration stage. Further, a proportional valve or a throttle is arranged in the substitute line downstream of the second filtration stage.

In certain exemplary embodiments according to the present invention, the conveying devices which are referred to in connection with the exemplary embodiments according to the present invention described herein, such as a pump, a pressure pump, a flow pump or a volume pump or the like as well as the flow limitation devices which are also referred to in connection with the exemplary embodiments according to the present invention described herein, such as a throttle, a flow divider valve, a proportional valve, a tube squeeze valve or the like are configured, controlled, regulated or used for dosing the substitute, in particular based on the information about the desired substitute flow or the desired substitute volume.

In some exemplary embodiments according to the present invention, a pressure pump is arranged in the substitute line downstream of the second filtration stage.

In some exemplary embodiments according to the present invention, a temperature sensor and/or a particle filter is arranged in the substitute line downstream of the pressure pump.

In some exemplary embodiments according to the present invention, a bypass line branches off the substitute line. It may be connected with the dialysate drain line.

In certain exemplary embodiments according to the present invention, the second filtration stage is integrated in the dialysis liquid supply line or the dialysis liquid flows through the second filtration stage (i.e. it is accordingly arranged). Thereby, a volume pump is arranged in the substitute line downstream of the second filtration stage.

In some exemplary embodiments according to the present invention, a substitute pressure sensor is arranged in the substitute line upstream of the volume pump. In some exemplary embodiments according to the present invention, a particle filter and/or a pressure sensor is arranged downstream of the volume pump.

In certain exemplary embodiments according to the present invention, at least one flow sensor is arranged in the dialysis liquid supply line and/or in the substitute line.

In some exemplary embodiments according to the present invention, as described above, a branch line which downstream of the branch point leads, heads or supplies fluid into the second filtration stage branches off the dialysis liquid supply line at a branch point, wherein the substitute line emerges from the second filtration stage, in particular directly or indirectly. In these exemplary embodiments, the substitute line is located downstream of the second filtration stage. The substitute line does not start in front or upstream of the second filtration stage. The share of the dialysis liquid which is supplied to the dialyzer does not flow through the second filtration stage.

In some exemplary embodiments according to the present invention, a flow divider valve is arranged in the branch point and thus upstream of the second filtration stage.

In certain exemplary embodiments according to the present invention, at least one proportional valve is arranged in the dialysis liquid supply line downstream of the branch point.

In some exemplary embodiments according to the present invention, at least one proportional valve or at least one throttle is arranged in the branch line upstream of the second filtration stage.

In certain exemplary embodiments according to the present invention, a pre-pressure pump is arranged in the branch line downstream of the branch point.

In some exemplary embodiments according to the present invention, a temperature sensor is arranged in the branch line downstream of a pre-pressure pump which is located in the branch line.

In certain exemplary embodiments according to the present invention, a volume pump is arranged in the branch line downstream of the branch point.

In some exemplary embodiments according to the present invention, a branch pressure sensor is provided in the branch line downstream of the volume pump, but upstream of the second filtration stage.

In certain exemplary embodiments according to the present invention, a pre-pressure pump is arranged in the branch line upstream of the branch point.

In some exemplary embodiments according to the present invention, a flush line branches off the second filtration stage.

In certain exemplary embodiments according to the present invention, at least one flow sensor is arranged in the substitute line and/or in the dialysis liquid supply line downstream of the branch point and/or downstream of the second filtration stage and/or in the branch line.

In certain exemplary embodiments according to the present invention, the blood treatment apparatus is embodied as hemodialysis apparatus, hemofiltration apparatus or hemodiafiltration apparatus.

In some exemplary embodiments according to the present invention, the medical functional apparatus is embodied as blood cassette or as extracorporeal blood tube or blood tube set.

In some exemplary embodiments according to the present invention, the medical functional apparatus is a one-way or disposable article.

In certain embodiments according to the present invention everything related to or said with regard to "dosing" is also valid for "creating" or "providing."

In some embodiments according to the present invention introducing the substitute into the extracorporeal blood circuit is not part of the method according to the present invention.

In certain embodiments according to the present invention the devices according to the present invention comprise the devices, parts or components necessary for executing the method according to the present invention, particularly valves, conveying devices as pumps, regulating devices, controlling devices, etc.

Wherever herein there is mention of a sensor such as a pressure, temperature or flow sensor, according to the present invention each apparatus which is suitable and used to determine or measure the specific parameter is addressed.

Wherever herein there is mention of a substitute line or a substitute, according to the present invention a line arrangement for producing a different, in particular highly purified liquid can be understood. It can for example be provided or used as rinsing liquid for cleaning or desorbing loaded adsorber cartridges (by or across which for example blood plasma is conducted during a blood treatment). Such-like rinsing liquids which can also be produced as described herein, are usually not denoted as substitutes. On the basis of the before-mentioned, the present invention is therefore not to be limited to substitute. Any other liquid produced or dosed as described herein is also encompassed by the present invention. This applies also to the methods and apparatuses according to the present invention which are used therefore. Therefore, the present invention may for example also be used for dosing a rinsing liquid which is suitable for blood contact for cleaning or desorbing loaded adsorber cartridges.

Some or all exemplary embodiments according to the present invention may provide for one, several or all of the advantages named above and/or hereafter.

One advantage may be that in exemplary embodiments in which besides the present invention also a conventional dosing apparatus such as known from the state of the art and mentioned in the introduction is used, the process stability can be increased already due to the dosing of the substitute which takes place by the hydraulic system according to the present invention. Errors of the conventional dosing apparatus cannot result in an overdosing of substitute.

Another advantage may be that a dosing device does not have to be provided with apparatuses according to the present invention or their use any more. Rather, the dosing takes place with the desired precision by the hydraulic system of the blood treatment apparatus according to the present invention. This saves the costs for providing a dosing device which is specifically provided for dosing the substituate. Further, this can help save efforts for mounting, calibrating, monitoring and maintaining the dosing apparatus which is not required any more according to the present invention, as well as the costs which are hereby incurred.

By transferring the step of dosing the substituate to the blood treatment apparatus, the precision of dosing can furthermore be ensured in a more reliable way than it is possible with state-of-the-art solutions in which dosing is partially or completely transferred to a blood tube set or a blood cassette, i.e., one-way articles.

Another advantage may be that by the present invention conveying may take place with high precision, or even with a higher precision than before, as far as the conveyed volume is concerned. One reason for this may be that some of the tolerances which can each reduce the precision may be omitted. This applies for example to the compliance of the substitute tube and/or to the spring load of the roller pump.

BRIEF DESCRIPTION OF THE DRAWINGS

The present invention is hereafter exemplarily explained with reference to the appended figures in which identical reference numerals refer to same or similar components. In the partially highly simplified figures it applies that.

DETAILED DESCRIPTION

Figure 1:
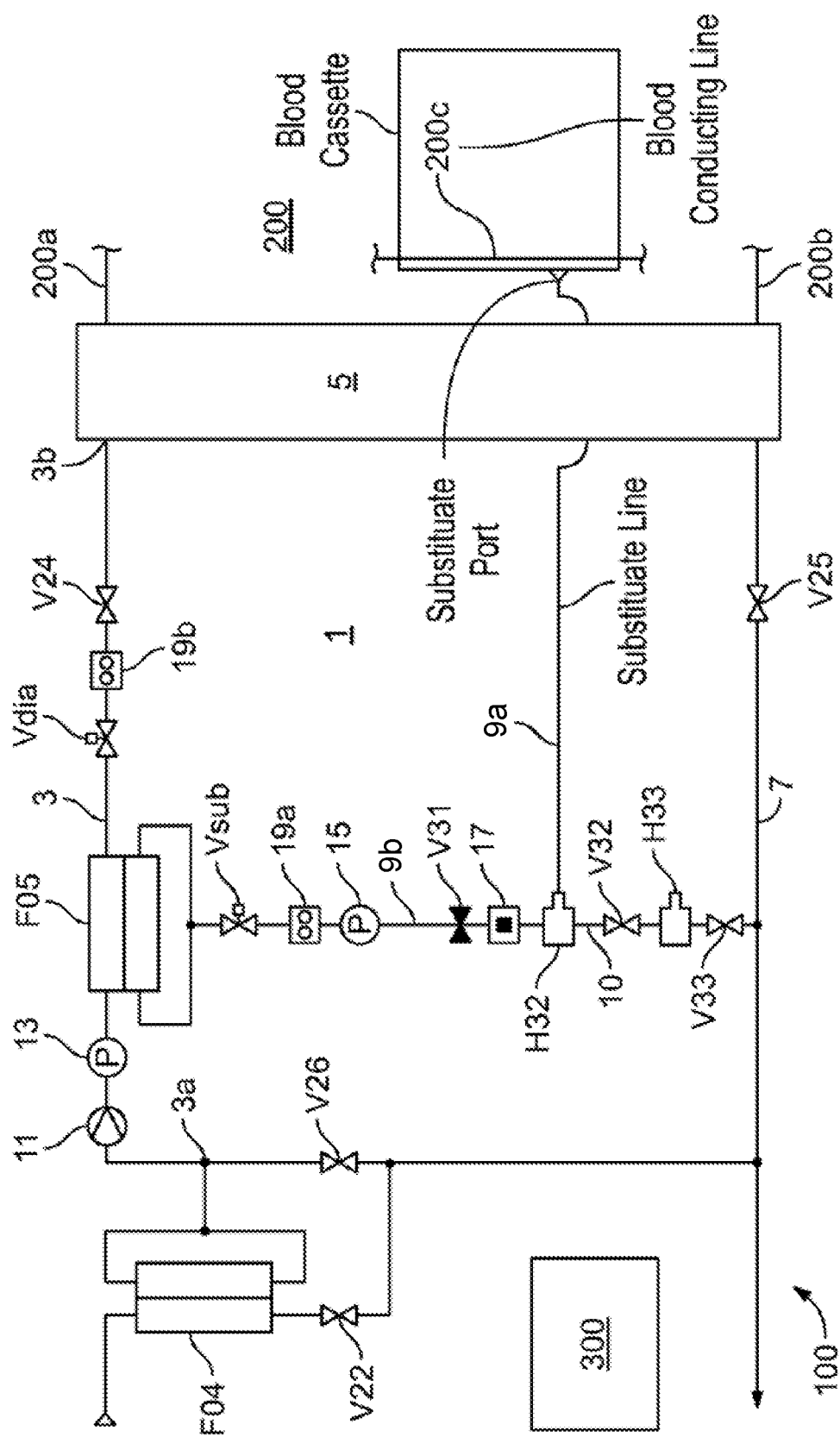
FIG. 1 shows in a schematically simplified way and in extracts the hydraulic system of the blood treatment apparatus according to a first exemplary embodiment according to the present invention.

FIG. 1 shows in a schematically simplified way a hydraulic system 1 according to the present invention of a treatment apparatus 100 according to the present invention by which the method according to the present invention can be executed, and a blood circuit 200 which is only indicated schematically as an example of a medical functional apparatus.

The hydraulic system 1 comprises a dialysis liquid supply line 3, also denoted as dialysate line, which leads dialysis liquid which was produced online, i.e. by the treatment apparatus 100, to a blood filter or dialyzer 5. As dialysis liquid supply line 3 the whole line is understood herein through which dialysis liquid flows, which extends from a junction 3a downstream from a first filter F04 which is also denoted as first filtration stage up to the entry of the dialysis liquid supply line 3 at an entry site 3b into the dialyzer 5.

A dialysate drain line 7 attaches to the dialyzer 5 which discharges the dialysis liquid from the dialyzer 5. The dialysis liquid which is supplied to the dialyzer 5 by the dialysis liquid supply line 3 passes not only through the first filter F04 but also trough a second filter F05, which is also denoted as second filtration stage, before it enters the dialyzer 5. The second filter F05 is integrated in the dialysis liquid supply line 3 and dialysis liquid flows through it. Dialysate can flow through the second filter F05 along the dialysis liquid supply line 3 without being filtered.

In the second filter F05 thus a filtrate is produced which hereafter is also denoted as "substituate" which, being a share or portion of the dialysis liquid, is filtrated, lead through or pressed through the membrane or sterile membrane of the second filter F05 and lead into a second substituate line 9b. From the second substituate line 9b, the substituate which is produced this way may for example be supplied via a substituate port to an extracorporeal blood circuit 200, which may partially run on a blood cassette which is not illustrated. This may optionally take place in predilution and/or postdilution. The extracorporeal blood circuit 200, which is only schematically indicated in the appended figures, comprises at least one blood drain line 200a which is connected to the dialyzer 5, a blood supply line 200b which is also connected to the dialyzer 5, and a section 200c, which is in direct fluid connection with a first substituate line 9a.

A clamp or a valve V24 is optionally integrated in the dialysis liquid supply line 3. A clamp or a valve V25 is optionally integrated in the dialysate drain line 7. A clamp or a valve V31 is optionally integrated in the second substituate line 9b between the second filter F05 and the substituate port H32.

A connection line 10 attaches to the substituate port H32. It connects the first substituate line 9a and the second substituate line 9b with the dialysate drain line 7. Further valves V32 and V33, which are also only optionally provided, are shown in the connection line 10 in FIG. 1. A retention valve V22, a bypass valve V26 and a flush port H33 are also optionally provided.

Between the first filter F04 and the second filter F05, a pre-pressure pump 11 and a dialysate pre-pressure sensor 13 may be, each optionally, provided. Equally, a substituate pressure sensor 15 and a blood detector 17 may be, each optionally, provided in the second substituate line 9b.

According to the present invention, if there is mention of a "pre-pressure," the respective element—such as the pre-pressure pump 11 or the dialysate pre-pressure sensor 13—is arranged or acts upstream of the second filter F05.

For dosing the substituate flow or substituate volume, a first proportional valve Vdia, which is integrated in the dialysis liquid supply line 3, and a second proportional valve Vsub, which is integrated in the second substituate line 9b are provided in the first exemplary embodiment illustrated in FIG. 1. It has to be noted that the elements Vdia and Vsub are only exemplarily proportional valves. They can also be embodied as other suitable flow or stream limitation devices which are known to the person skilled in the art. The valve position or valve positions are controlled or regulated in the exemplary embodiment shown in FIG. 1 such that the desired flow separation between the dialysis liquid flow in the dialysis liquid supply line 3 and substituate flow in the second substituate line 9b is achieved.

In case it has to be ensured that the dialysate pre-pressure which for example can be measured with the dialysate pre-pressure sensor 13 does not fall below a defined or predetermined pressure value, the valve position of one of the two proportional valves Vdia and Vsub or the valve positions of both proportional valves Vdia and Vsub can be accordingly set or regulated. This predetermined pressure value may be determined such that both in the dialysis liquid supply line 3 and in the second substituate line 9b defined flows can be ensured. An optionally provided upper pressure limitation may take place by the hydraulic system. When falling below a minimum pressure, closing the second substituate line 9b, for example by the valve V31, can optionally take place as a safety measure.

Alternatively or additionally, a desired pre-pressure can be generated or ensured by a pump, for example by the optionally provided pre-pressure pump 11.

Optionally, a flow sensor 19b in the dialysis liquid supply line 3 and/or a flow sensor 19a in the second substituate line 9b are further provided for monitoring the achieved or the desired flow separation. Thereby, the flow sensor 19a is located downstream of the valve Vsub, the flow sensor 19b is located downstream of the valve Vdia. It is noted that according to the present invention, contrary to the exemplary embodiment as described herein, one, some or all of the flow sensors may alternatively be also located upstream of the proportional valves, regardless of the location of the remaining flow sensors, as long as they are located downstream of the branch point of dialysate and substituate or the branch point of the branch line.

The desired flow separation may optionally be monitored and ensured by corresponding pressure measurements and the pressure measurement apparatuses which are optionally provided herefor. In this case, it may be advantageously possible to do without the optionally provided flow sensors 19a and 19b.

If the valve Vsub is embodied as a tube squeeze valve, as is provided in further exemplary embodiments according to the present invention, the additional provision of a valve V31 in the second substituate line 9b may be waived. In such case, a flow sensor can be advantageously used. With it, a desired conveying rate precision of for example 10% can be easily checked and optionally readjusted accordingly.

The explanations made with respect to FIG. 1 also apply to the following figures, where seen as useful by the person skilled in the art. This applies in particular to the elements shown in FIG. 1, their designations, and their functions.

For controlling or regulating the above-named components of the hydraulic system 1 in order to execute the method according to the present invention the blood treatment apparatus 100 comprises a regulating or control apparatus 300 according to the present invention, or it is connected herewith in signal or operative connection.

FIG. 2 shows again in a schematically simplified way and only in extracts the hydraulic system 1 of the blood treatment apparatus 100 in a second exemplary embodiment according to the present invention. In the setup or arrangement shown in FIG. 2, a throttle 21 is again merely optionally provided at the site at which the valve Vsub is shown in FIG. 1 instead of the valve Vsub which is optionally embodied as proportional valve. Apart from that, the setup of FIG. 2 may be the one of FIG. 1.

Figure 2:
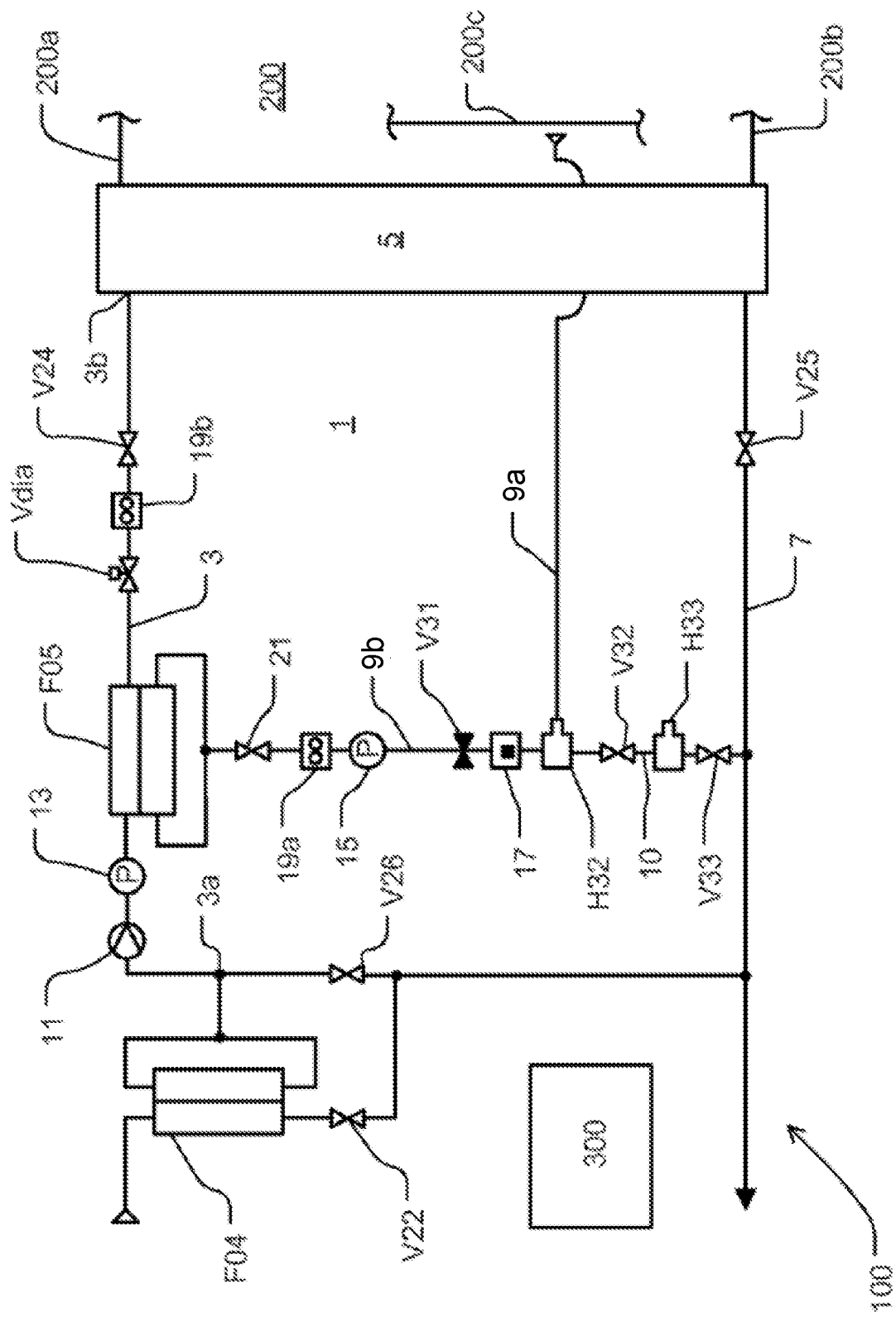
FIG. 2 shows in a schematically simplified way and in extracts the hydraulic system of the blood treatment apparatus according to a second exemplary embodiment according to the present invention.

The exemplary embodiment according to the present invention which is disclosed with regard to FIG. 2, in which only one proportional valve, that is the valve Vdia, is provided may be appropriate especially if it can be ensured that the pressure drop across the second substituate line 9b or the whole substituate branch is always higher than across the dialysis liquid supply line 3 or the whole dialysate branch. If this is the case, which always has to be assumed in a hemodiafiltration treatment as otherwise no dialysate would flow anymore and the treatment would become a hemofiltration treatment, one proportional valve can be saved as shown in FIG. 2.

It is assumed that the pressure drop across the substituate branch should usually be higher than across the dialysate branch as the dialysis liquid which remains in the dialysis liquid supply line passes through the second filter F05 in a longitudinal direction and the share of the dialysis liquid which is discharged into the substituate branch however has to be pressed through the membrane of the second filter F05.

Furthermore, usually a non-return valve which is present on a disposable such as a blood cassette or the extracorporeal blood circuit and which is not shown here is located in the substituate branch for preventing a return flow. This non-return valve comprises a cracking pressure or opening pressure to ensure the blocking function of the non-return valve. Thus, the pressure drop across the substituate branch is higher. The opening pressure may exemplarily be more than 100 mbar.

If it has to be ensured that the pressure drop across the substituate branch is higher than the pressure drop across the dialysis liquid branch, the substituate branch may be furnished with a throttle 21 as shown in FIG. 2. In its setup, the maximum admissible substituate flow as well as the maximum or maximum admissible dialysate pre-pressure can be considered.

Figure 3:
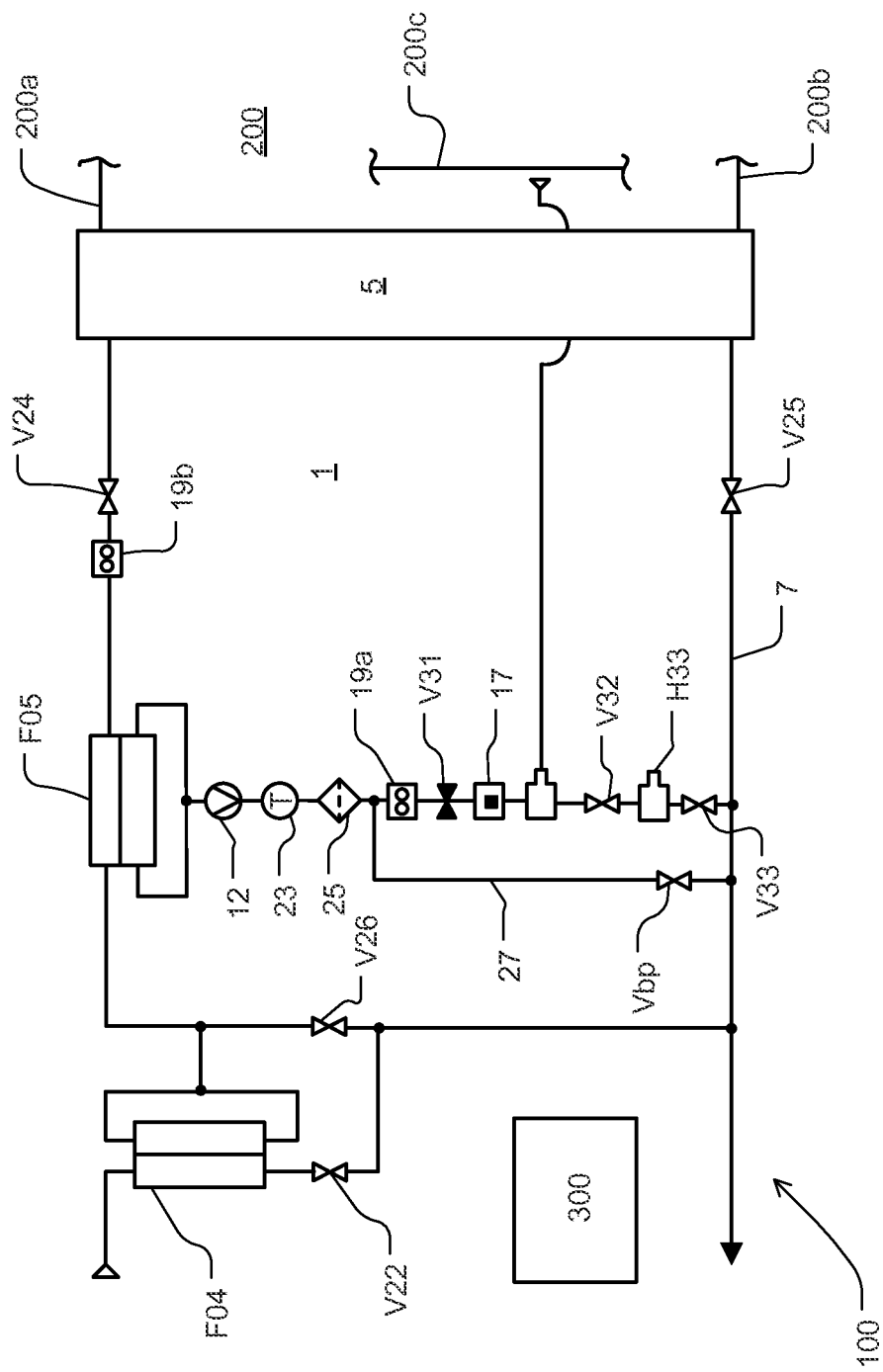
FIG. 3 shows in a schematically simplified way and in extracts the hydraulic system of the blood treatment apparatus according to a third exemplary embodiment according to the present invention.

FIG. 3 shows a third exemplary embodiment according to the present invention. The explanations to it substantially correspond to those made with regards to FIGS. 1 and 2. Compared to the illustrations of FIGS. 1 and 2, however, a pump 12 which is located downstream of the second filter F05 is arranged in the second substituate line 9b instead of the pre-pressure pump 11 located upstream from the second filter F05. Furthermore, a temperature sensor 23 and/or a particle filter 25 may optionally be provided downstream from the pump 12, which may for example be embodied as a pressure pump. Based on the temperature values provided by the temperature sensor 23 it can be ensured that the substituate supplied to the blood circuit 200 has not been heated up to an inadmissible extend, which could have taken place by the pump 12 upstream from it. Should an inadmissible heating be detected, the heated substituate may completely or partly be discharged via an optionally provided bypass line 27 by opening an arranged bypass valve Vbp.

FIG. 4 shows again in a schematically simplified way and only in extracts the hydraulic system 1 of the blood treatment apparatus 100 in a fourth exemplary embodiment according to the present invention.

Figure 4:
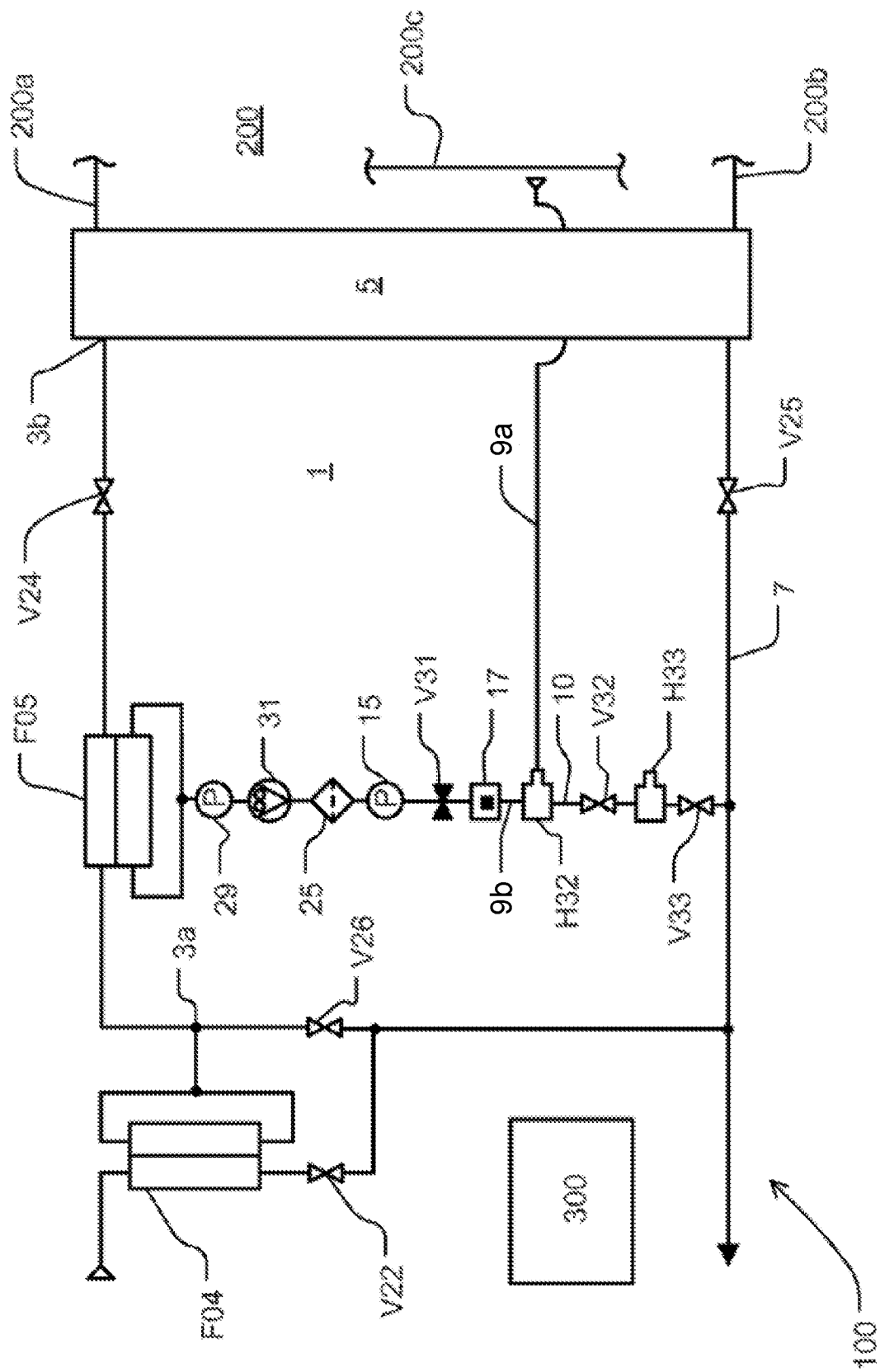
FIG. 4 shows in a schematically simplified way and in extracts the hydraulic system of the blood treatment apparatus according to a fourth exemplary embodiment according to the present invention.

In the exemplary embodiment of FIG. 4, a substituate pre-pressure sensor 29 is optionally provided in the second substituate line 9b downstream of the second filter F05. Instead of a pre-pressure pump 11 which is provided in the dialysis liquid supply line 3, in the exemplary embodiment of FIG. 4 a volume pump 31 is provided in the second substituate line 9b. There, it is located downstream of the second filter F05 and—if available—downstream of the substituate pre-pressure sensor 29.

Also in the exemplary embodiment shown in FIG. 4 a particle filter 25 may be optionally provided. It can be arranged downstream of the volume pump 31.

In addition, the second substituate line 9b comprises a substituate sensor 15. It is located downstream of the volume pump.

FIGS. 5 to 8, which are discussed hereafter, show further exemplary embodiments according to the present invention which differ from the ones of FIGS. 1 to 4 in that the second filter F05 is not a part of the dialysis liquid supply line 3. In fact, different to what has been discussed regarding FIGS. 1 to 4, the dialysis liquid which enters the dialyzer 5 does not also flow through the second filter F05. In the arrangements of FIGS. 5 to 8, only the share of dialysis liquid which is produced online by the first filter F04 flows through the second filter F05, which is used for the production of filtrate or substituate.

In the arrangements of FIGS. 5 to 8, this takes place in that a branch line 35 which starts at a branch point 35a is provided between the dialysis liquid supply line 3 and the second filter F05.

FIG. 5 shows again in a schematically simplified way and only in extracts the hydraulic system 1 of the blood treatment apparatus 100 in a fifth exemplary embodiment according to the present invention.

In contrast to what is illustrated in the preceding figures, a flow divider valve 37 which is provided at a branch point 35a ensures that the volume flow which flows through the first filter F04 and which optionally is conveyed through a pre-pressure pump 11 is separated in the desired ratio into a dialysate flow and a branch or substituate flow. By integrated pressure compensators, this flow ratio can be maintained independently from the respective counter-pressure. For ensuring the function, the pre-pressure pump 11 which is optionally provided upstream of the flow divider valve 37 can supply the pre-pressure required to operate the flow divider valve 37. The arrangement of FIG. 5 comprises a flush line 28 which contains a flush valve VF1.

Figure 5:
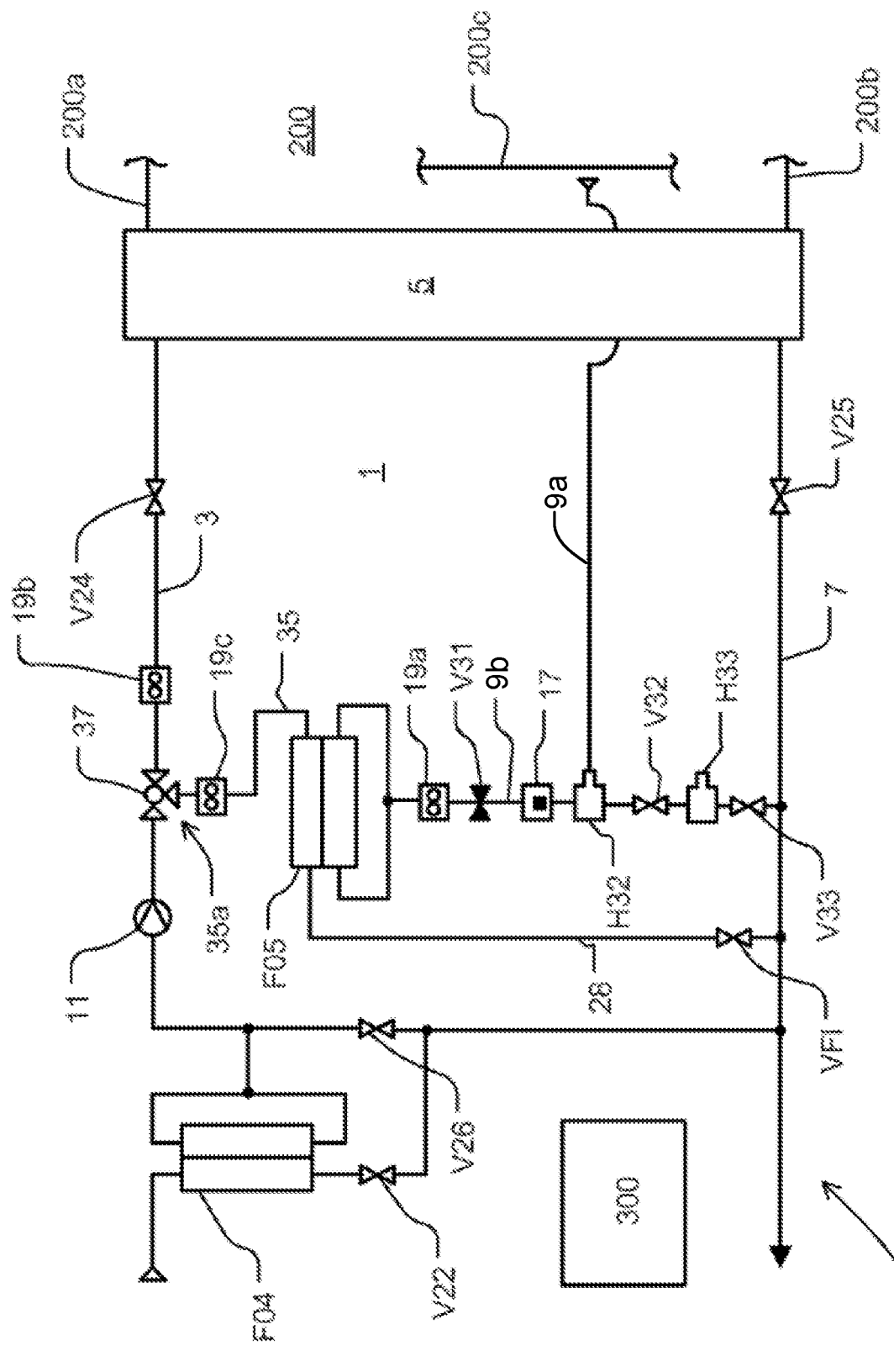
FIG. 5 shows in a schematically simplified way and in extracts the hydraulic system of the blood treatment apparatus according to a fifth exemplary embodiment according to the present invention.

Other than the preceding figures, FIG. 5 comprises a third flow sensor 19c which is only optionally provided, which is arranged in the branch line 35. The third flow sensor 19c may optionally be provided together with the first flow sensor 19a or the second flow sensor 19b or both flow sensors 19a and 19b. According to the present invention, it also suffices to provide only one of the flow sensors 19a, 19b and 19c or arbitrary combinations hereof, for example at the sites of the hydraulic system 1 shown in FIG. 5.

Figure 6:
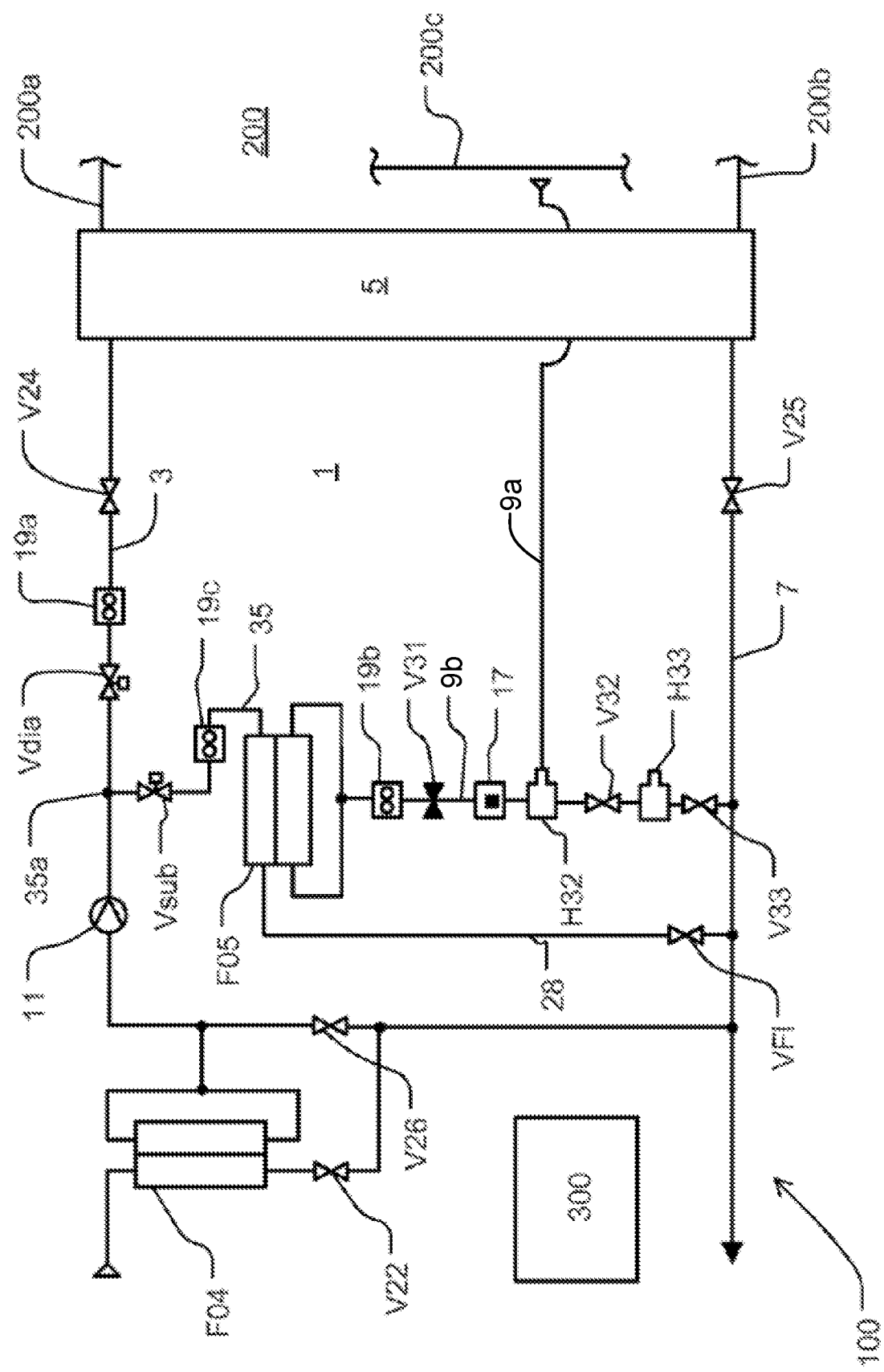
FIG. 6 shows in a schematically simplified way and in extracts the hydraulic system of the blood treatment apparatus according to a sixth exemplary embodiment according to the present invention.

FIG. 6 just as FIG. 5 again shows in a schematically simplified way the hydraulic system 1 in a sixth exemplary embodiment according to the present invention.

The flow separation is achieved in FIG. 6 again with two proportional valves Vdia and Vsub as illustrated. The advantages associated herewith encompass reduced mechanical complexity and an improved cleaning possibility by staff and/or machine.

Figure 7:
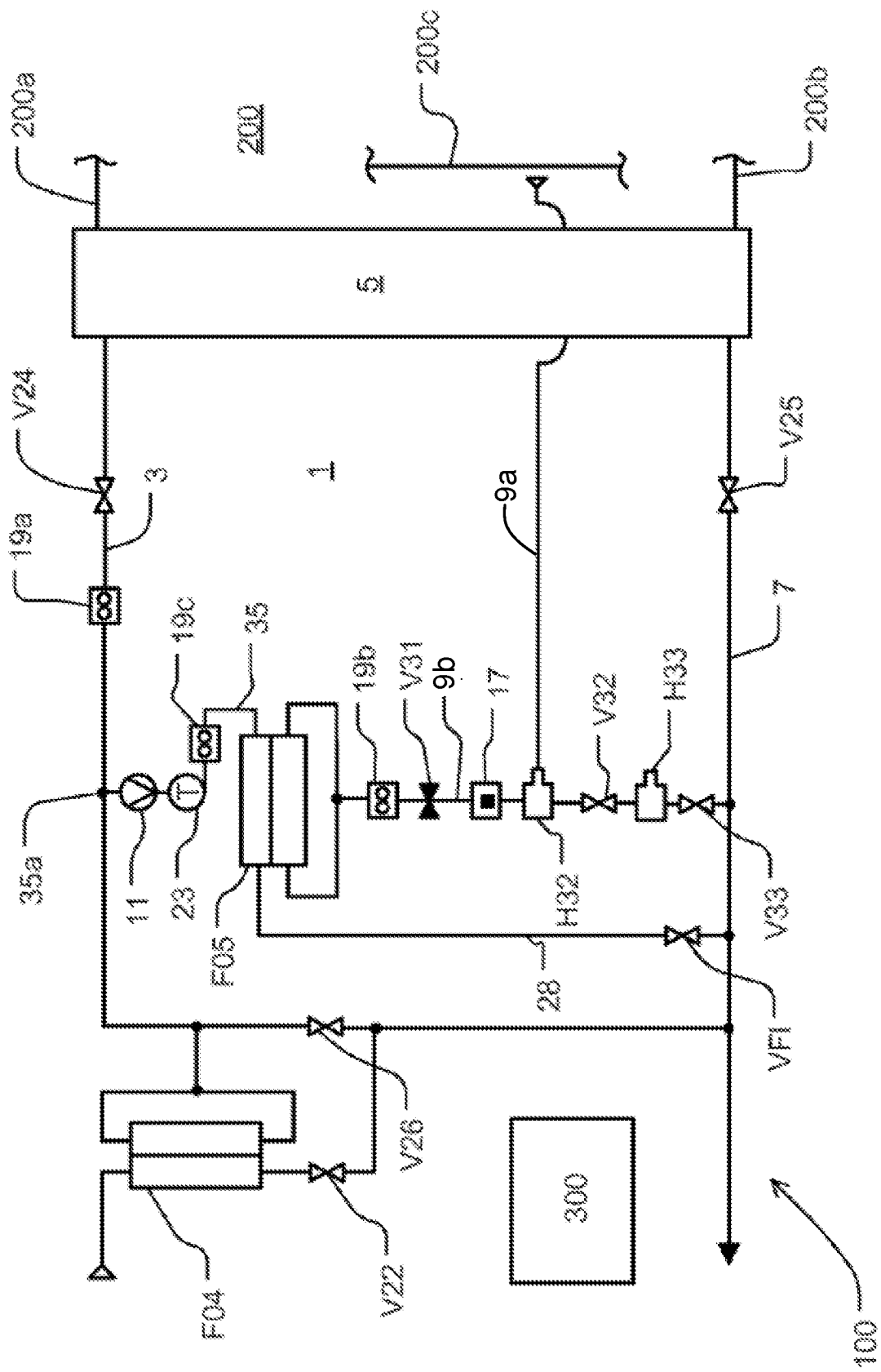
FIG. 7 shows in a schematically simplified way and in extracts the hydraulic system of the blood treatment apparatus according to a seventh exemplary embodiment according to the present invention.

FIG. 7 shows a seventh exemplary embodiment according to the present invention. In this exemplary embodiment, a pre-pressure pump 11 is provided, preferably in the branch line 35, which with the support of one or several flow sensors 19a, 19b and 19c can be regulated to achieve the desired substituate flow. The pressure pump or pre-pressure pump 11 may for example be a geared pump having a bypass or a centrifugal pump.

As for example a centrifugal pump can significantly heat up the substituate, a temperature sensor 23 may optionally be provided downstream of the pre-pressure pump 11 for monitoring the temperature of the substituate. According to the present invention, it can be provided that when an excess temperature is detected or when a predetermined temperature limit value is exceeded, substituate that has been heated too much can be discharged via the flush valve VF1 and the flush line 28. The valve V31 can be completely or partially closed for this purpose.

Figure 8:
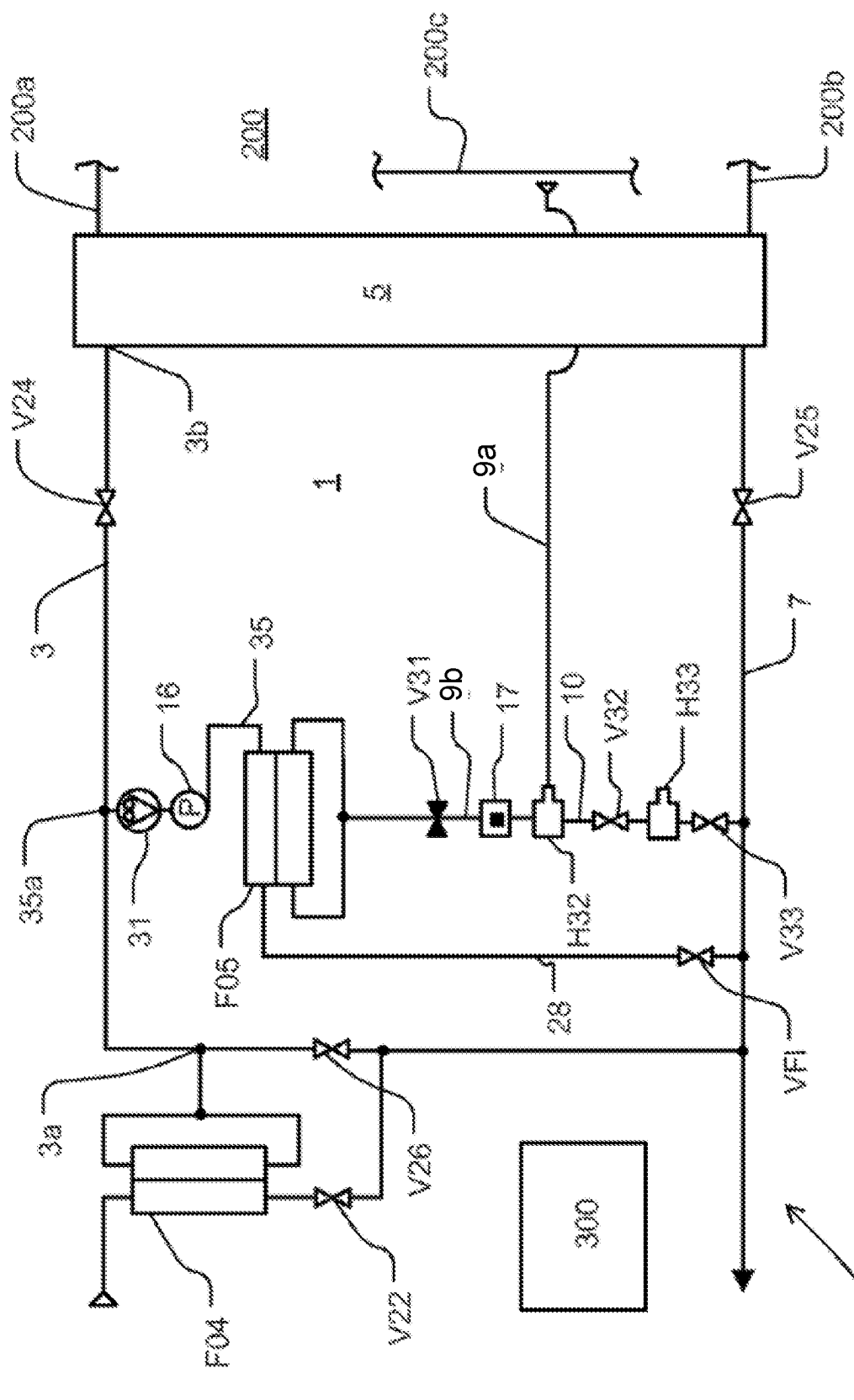
FIG. 8 shows in a schematically simplified way and in extracts the hydraulic system of the blood treatment apparatus according to an eighth exemplary embodiment according to the present invention.

FIG. 8 shows the hydraulic system 1 according to the present invention of a treatment apparatus 200 according to the present invention according to an eighth exemplary embodiment according to the present invention.

In this exemplary embodiment, a volume pump 31 is provided, preferably in the branch line 35. It can generate a predefined substituate flow. The volume pump or flow pump 31 may for example be designed as a gear pump without bypass, a membrane pump, a tube roller pump or also as a rotary vane pump.

In this or similar exemplary embodiments according to the present invention, the pressure may be monitored by a suitable pressure measurement apparatus such as for example the branch line pressure sensor 16 for limiting the pressure in the branch line 35 depending on the utilized pump type.

Some of the features of the exemplary embodiments according to the present invention which are illustrated in the figures can be taken from the following Table 1:

TABLE 1

| feature | FIG. 1 | FIG. 2 | FIG. 3 | FIG. 4 | FIG. 5 | FIG. 6 | FIG. 7 | FIG. 8 |
|---|---|---|---|---|---|---|---|---|
| conventional switching of the second filtration stage in dialysis liquid supply line | yes | yes | yes | yes | no | no | no | no |
| second filtration stage in branch line of the dialysis liquid supply line | no | no | no | no | yes | yes | yes | yes |
| flush line at the outlet of the dialysate chamber of the second filtration stage | no | no | no | no | yes | yes | yes | yes |
| bypass line branching off the filtrate line to the flush | no | no | yes | no | no | no | no | no |
| flow divider valve in dialysis liquid supply line downstream of first filtration stage | no | no | no | no | yes | no | no | no |
| proportional valve in dialysis liquid supply line downstream of second filtration stage | yes (opt.) | yes | no | no | no | yes (opt.) | no | no |

TABLE 1-continued

| feature | FIG. 1 | FIG. 2 | FIG. 3 | FIG. 4 | FIG. 5 | FIG. 6 | FIG. 7 | FIG. 8 |
|---|---|---|---|---|---|---|---|---|
| proportional valve in substituate line downstream of second filtration stage | yes (opt.) | no | no | no | no | no | no | no |
| flow measurement in dialysis liquid supply line | yes (opt.) | yes (opt.) | yes (opt.) | no | yes (opt.) | yes (opt.) | yes (opt.) | no |
| flow measurement in branch line upstream of the second filtration stage | no | no | no | no | yes (opt.) | yes (opt.) | yes (opt.) | no |
| flow measurement in substituate line downstream of the second filtration stage | yes | yes (opt.) | yes (opt.) | no | yes (opt.) | yes (opt.) | yes (opt.) | no |
| pre-pressure pump in dialysis liquid supply line downstream of the first filtration stage | yes | yes | no | no | yes | yes | no | no |
| pre-pressure measurement in dialysis liquid supply line downstream of the first filtration stage | yes | yes | no | no | no | no | no | no |
| pre-pressure pump in branch line upstream of the second filtration stage | no | no | no | no | no | no | yes | no |
| pressure pump in substituate line downstream of the second filtration stage | no | no | yes | no | no | no | no | no |
| volume pump in branch line upstream of the second filtration stage | no | no | no | no | no | no | no | yes |
| volume pump in branch line downstream of the second filtration stage | no | no | no | yes | no | no | no | no |
| temperature sensor downstream of pressure pump | no | no | yes | no | no | no | yes | no |
| pressure monitoring downstream of volume pump | no | no | no | yes | no | no | no | yes |
| pre-pressure measurement upstream of volume pump | no | no | no | yes | no | no | no | no |
| particle filter in substituate line downstream of volume pump | no | no | no | yes | no | no | no | no |
| blood detector in substituate line (generally optional) | yes | yes | yes | yes | yes | yes | yes | yes |

REFERENCE NUMERAL LIST 1 hydraulic system of the treatment apparatus 100
3 dialysis liquid supply line
3a junction
3b entry site
5 dialyzer or filter
7 dialysate drain line
9a first substituate line
9b second substituate line
10 connection line
11 pre-pressure pump
12 pump
13 dialysate pre-pressure sensor
15 substituate pressure sensor
16 branch line pressure sensor
17 blood sensor
19a first flow sensor
19b second flow sensor
19c third flow sensor
21 throttle
23 temperature sensor 25 particle filter
27 bypass line
28 flush line
29 substituate pre-pressure sensor
31 volume pump
35 branch line
35a branch point
37 flow divider valve
100 treatment apparatus
200 extracorporeal blood circuit
200a blood drain line
200b blood supply line
200c section of the extracorporeal blood circuit 200 with direct fluid connection to the first substituate line 9a
300 control device or regulating device
V22 retention valve
V24 clamp or valve
V25 clamp or valve
V26 bypass valve
V31 valve in the substituate line
VF1 flush valve
Vbp bypass valve
Vdia valve in the dialysis liquid supply line
Vsub valve in the substituate line
F04 first filter
F05 second filter
H32 substituate port
H33 flush port

What is claimed is:

1. A medical system comprising:
 a blood treatment apparatus; and
 a medical functional apparatus, configured to operate with the blood treatment apparatus, wherein the medical functional apparatus is a blood cassette, an extracorporeal blood tube or a blood tube set, the medical functional apparatus comprising:
  a first substituate line; and
  a substituate port for receiving a substituate produced by the blood treatment apparatus,
  wherein the medical functional apparatus is free of any apparatus arranged or provided for dosing the substituate from the substituate line into a blood-conducting line;
 wherein the blood treatment apparatus comprises:
  a first filter,
  a second filter,
  a dialysis liquid supply line in fluid communication with the first filter,
  a second substituate line in fluid communication with the second filter, wherein the second substituate line emerges from the second filter and is arranged downstream of the second filter, and wherein the second substituate line is in fluid communication with the first substituate line of the medical functional apparatus when the first substituate line and the second substituate line are coupled to the substituate port,
  a flow sensor situated along the second substituate line,
  at least one conveying apparatus that is arranged downstream of the first filter along the dialysis liquid supply line and upstream of the second filter,
  at least one flow limitation device located along at least one of the dialysis liquid supply line and the second substituate line, wherein the at least one flow limitation device is a proportional valve or a throttle, and
  a control device programmed to control the blood treatment apparatus to:
   convey a fluid through the first filter of the blood treatment apparatus and into the dialysis liquid supply line, thereby generating a dialysis liquid which is suitable for use in a dialyzer connected to the dialysis liquid supply line;
   guide a portion of the dialysis liquid into the second substituate line that is in fluid communication with the second filter of the blood treatment apparatus, thereby generating substituate which is suitable for use in an extracorporeal blood circuit via the substituate port of the medical functional apparatus after the dialysis liquid passes through the second filter;
   monitor substituate flow in the second substituate line with the flow sensor situated along the second substituate line;
   operate the at least one conveying apparatus and the at least one flow limitation device to generate the substituate;
   based on the substituate flow in the second substituate line monitored by the flow sensor situated along the second substituate line, regulate the flow of the substituate by controlling the at least one conveying apparatus and the at least one flow limitation device to regulate a volume of a portion of the dialysis liquid which passes through the second filter to generate the substituate.

2. The system according to claim 1, wherein the blood treatment apparatus is or comprises a hemodialysis apparatus, a hemofiltration apparatus, or a hemodiafiltration apparatus.

3. The system according to claim 1, further comprising:
 a proportional valve or a throttle disposed in at least one of the dialysis liquid supply line or in the second substituate line downstream of the second filter,
 wherein the second filter is integrated in the dialysis liquid supply line.

4. The system according to claim 1, further comprising:
 a pressure pump disposed in the second substituate line downstream of the second filter,
 wherein the second filter is integrated in the dialysis liquid supply line.

5. The system according to claim 4, further comprising:
 at least one of a temperature sensor in the second substituate line downstream of the pressure pump, a particle filter in the second substituate line downstream of the pressure pump, or a bypass line branching off the second substituate line.

6. The system according to claim 1, further comprising:
 a volume pump in the second substituate line downstream of the second filter, wherein the second filter is integrated in the dialysis liquid supply line.

7. The system according to claim 6, further comprising:
 at least one of a substituate pressure sensor in the second substituate line upstream of the volume pump, a particle filter downstream of the volume pump, or a pressure sensor downstream of the volume pump.

8. The system according to claim 1, further comprising:
 at least one flow sensor disposed in the dialysis liquid supply line.

9. The system according to claim 1, further comprising:
 a branch line which branches off from the dialysis liquid supply line at a branch point, wherein the branch line, downstream from the branch point, leads into the second filter; and
 a flow divider valve in the branch point upstream of the second filter.

10. The system according to claim 1, further comprising:
a branch line which branches off from the dialysis liquid supply line at a branch point; and
at least one proportional valve or throttle,
wherein the branch line leads into the second filter downstream, and
wherein the at least one proportional valve is located in the dialysis liquid supply line downstream of the branch point, or the at least one proportional valve or throttle is located in the branch line upstream of the second filter.

11. The system according to claim 1, further comprising:
a branch line which branches off from the dialysis liquid supply line at a branch point; and
a pre-pressure pump,
wherein the branch line leads into the second filter downstream, and
wherein the pre-pressure pump is arranged in the branch line downstream of the branch point.

12. The system according to claim 11, further comprising:
a temperature sensor located in the branch line downstream of the pre-pressure pump.

13. The system according to claim 1, further comprising:
a branch line which branches off from the dialysis liquid supply line at a branch point;
a volume pump located in the branch line downstream of the branch point; and
a branch line pressure sensor,
wherein the branch line leads into the second filter downstream, wherein the branch line is located downstream of the branch point, and
wherein the branch line pressure sensor is located downstream of the volume pump but upstream of the second filter.

14. The system according to claim 1, further comprising:
a branch line which branches off from the dialysis liquid supply line at a branch point,
a pre-pressure pump, and
a flush line,
wherein the branch line leads into the second filter downstream,
wherein the pre-pressure pump is located upstream of the branch point, and
wherein the flush line branches off the second filter.

\* \* \* \* \*